United States Patent [19]

Schebece

[11] Patent Number: 5,258,174
[45] Date of Patent: Nov. 2, 1993

[54] CLEAR STICK ANTI-PERSPIRANT

[75] Inventor: Frank Schebece, Edison, N.J.

[73] Assignee: Colgate-Palmolive Company, New York, N.Y.

[21] Appl. No.: 496,571

[22] Filed: Mar. 21, 1990

[51] Int. Cl.$^5$ .......................... A61K 7/32; A61K 7/34; A61K 7/36; A61K 7/38

[52] U.S. Cl. ................................ 424/65; 424/DIG. 5; 424/66; 424/67; 424/68

[58] Field of Search ...................... 424/DIG. 5, 66, 67, 424/68, 65

[56] References Cited

U.S. PATENT DOCUMENTS

| | | | |
|---|---|---|---|
| 2,876,163 | 3/1959 | Garizio et al. | 167/90 |
| 3,255,082 | 6/1966 | Barton | 167/90 |
| 3,873,686 | 3/1975 | Beekman | 424/47 |
| 3,876,758 | 4/1975 | Beekman | 424/47 |
| 3,904,741 | 9/1975 | Jones | 423/462 |
| 3,989,805 | 11/1976 | Notari et al. | 423/462 |
| 4,005,189 | 1/1977 | Reese et al. | 424/65 |
| 4,011,311 | 3/1977 | Noomen et al. | 424/65 |
| 4,090,013 | 5/1978 | Ganslaw et al. | 526/15 |
| 4,154,816 | 5/1979 | Roehl et al. | 424/68 |
| 4,302,443 | 11/1981 | deNavarre et al. | 424/68 |
| 4,434,178 | 2/1988 | Hostettler et al. | 424/287 |
| 4,673,570 | 2/1988 | Soldati | 424/66 |
| 4,722,835 | 2/1988 | Schamper et al. | 424/66 |
| 4,722,836 | 2/1988 | Geary et al. | 424/68 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,853,214 | 8/1989 | Orr | 424/69 |

FOREIGN PATENT DOCUMENTS

| | | |
|---|---|---|
| 268137 | 5/1961 | Australia . |
| 0291334 | 5/1987 | European Pat. Off. . |
| 0272919 | 12/1987 | European Pat. Off. . |
| 0274267 | 12/1987 | European Pat. Off. . |
| 753063 | 3/1967 | Italy . |
| 1541396 | 2/1979 | United Kingdom . |

OTHER PUBLICATIONS

"Rehers Enhanced Efficiency Aluminum Chlorohydrates, A summary of their efficacy, chemical and physical properties and formulations".

"Studies of Hydrolyzed Aluminum Chloride solutions", The Journal of Physical Chemistry, vol. 84, No. 22, 1980.

Technical Bulletin of BASF Wyandotte Corporation, "Urethane Chemicals-Quadrol", Aug. 1984.

Handbuch Der Kosmetika Und Riechstoffe, III.Band: Die Korperpflegemittel, von Hugo Janistyn, pp. 684-687.

*Primary Examiner*—Dale R. Ore
*Attorney, Agent, or Firm*—Robert C. Sullivan; Richard J. Ancel

[57] ABSTRACT

A clear gel stick composition is provided from a formula comprising an antiperspirant metal salt, a mono- or di-carboxylic acid or salt of such acid as a complexing agent and a hardening agent selected from the group consisting of lower alkanol amines, diamines and amides.

7 Claims, No Drawings

CLEAR STICK ANTI-PERSPIRANT

BACKGROUND OF THE INVENTION

This invention relates to the provision of a clear gel antiperspirant stick containing an anti-perspirant metal salt and, in particular, containing aluminum chlorhydrate. More specifically this invention relates to providing a clear gel anti-perspirant stick which is the reaction product of a metal salt having anti-perspirant properties with the salt of an organic acid and with a hardening agent.

Formulations for stick antiperspirants fall into three main categories i.e., compressed powder sticks, gel sticks and wax sticks. Each of these categories have advantages in certain situations but each have definite disadvantages. Compressed powder sticks for example are frequently brittle and hard and leave a cosmetically unacceptable greasy or tacky residue upon application. Not infrequently, wax based formulations yield cosmetically unacceptable products due to such factors as hardness, greasiness and stickiness. An improvement in wax based compositions was developed with the advent of certain soap alcohol gel sticks which were used in various cosmetic preparations and when rubbed on the skin left a thin even residue which was not greasy or tacky. Unfortunately, while such material is satisfactory for a wide range of cosmetic compositions, the soap alcohol gels have proven to be unsatisfactory for applying metallic astringent compositions such as those including aluminum chlorhydrate. It is believed that the metallic ion component of the aluminum chloride complex is sensitive to the soap component which inactivates the ion.

The art has long searched for a solution to the problem of producing a clear gel stick incorporating metallic anti-perspirant materials. In U.S. Pat. No. 4,673,570 to Soldati there is described a gel anti-perspirant composition made up of a volatile silicone fluid, a silicone emulsifier and other ingredients. Unfortunately, the use of such silicone compounds are expensive and have not been satisfactory. In U.S. Pat. No. 4,722,835 to Schamper et. al., a gelled transparent stick is described which contains an acidic anti-perspirant active component gelled in the presence of dibenzyl monosorbitol acetal (DBMSA). It has been discovered that gel sticks made up from this formulation tend to be unstable and not suitable for products which must be shipped and stored for long periods of time. In U.S. Pat. No. 3,255,082 to Barton, a method of preparing a stable aluminum chlorhydrate alkaline metal or alkaline earth metal salt complex is described for the purpose of preparing gels. While the teachings of this patent proports to overcome the difficulties described above with respect to prior art suggestions, it has been found that consistent production of stable gels is not possible using these methods. In U.S. Pat. No. 2,876,163 to Garizio, et al., there is described a method for preparing aluminum chlorohydroxy "alcogel" by combining an aluminum chlorohydroxy complex with an alkaline compound in an alcohol solvent. Taught therein, among the alkaline compounds, is ammonium acetate. While indeed, the combination of ammonium acetate with the aluminum chlorohydroxy complex form gels, it has been discovered that the gelation time is extremely long, that gels formed thereby tend to be unstable and after a period of time break down, and hence the process is not completely satisfactory for commercial production of gelled anti-perspirant sticks.

Accordingly, there is a need for providing a stable, clear gelled antiperspirant stick and a method for making the same.

SUMMARY OF THE INVENTION

It has now been discovered that a stable, clear gel stick incorporating, as the anti-perspirant agent such metallic anti-perspirants as aluminum chlorohydroxy complexes, may be provided and may be made by a controllable process which will consistently form such stable, clear, gel sticks. Specifically, such gel sticks may be made by first providing a reaction mixture comprising about 3 to about 30% by weight of anti-perspirant metal salt; from 3 to about 15% by weight, of a mono- or dicarboxylic acid having two to four carbon atoms or of the salts of such acid and preferably an acid or the salt of an acid selected from the group consisting of acetic, propionic, oxalic, malonic, succinic, tartaric acids and their salts; and about 0.1 to about 5% by weight, of a hardening agent selected from the group consisting of lower alkanol amines, diamines, and amides, wherein said amines, diamines, and amides comprise at least two alkanol groups. It has been discovered that the presence of the hardening agent in this reaction mixture, when reacted in accordance with the teachings herein, will allow for the formation of a gel stick which is both clear and stable and suitable for use. In contrast therewith, in the absence of the hardening agent, long periods of time are required for gelation and the resulting product tends to be unstable and frequently separates into different phases resulting in an unsuitable product for this purpose. While the explanation for this efficacy of the hardening agent is not well understood, it is theorized that the hardening agent either acts in a catalytic manner or as a cross-linking agent in view of its poly functional structure.

The anti-perspirant metallic salts of this invention may be any of the well known antiperspirant metal salts of aluminum, zinc, zirconium and zirconium aluminum mixtures of, for example, sulphates chlorides, chlorohydroxides, alums, formates, lactates and benzyl sulfonates phenol sulfonate as have been used in prior anti-perspirant compositions. Preferably the anti-perspirant metallic salt of choice is aluminum chlorohydrate. This antiperspirant metal salt and a method for making the same is described in U.S. Pat. No. 3,904,741 to Jones et al. Such compounds have the general formula $Al_2(OH)_xCl_{(6-x)}$ where in x is an integer or non-integer between 0 and 6 such that the material in question may be a mixture of varied proportions of such compounds as $Al_5OH_5Cl_{14}$, $Al_2OH_4Cl_2$, and $Al_5OH_5Cl$. The antiperspirant metallic salt should be present in the reaction mixture in a proportion of about 3 to 30%, by weight, and preferably from 10 to 20%, by weight.

The reaction mixture further includes as a complexing agent, an organic acid or derivatives thereof that are capable of forming complexes with the anti-perspirant metallic salt. Examples of such suitable complexing agents include acetic acid, propionic acid, oxalic acid, malonic acid, succinic acid and tartaric acid together with their cosmetically acceptable salts.

Such complexing agents are present in a proportion of about 3 to 15% by weight of the reaction mixture and preferably about 5 to about 10%, by weight of the reaction mixture. The complexing ingredient of choice is ammonium acetate.

In accordance with the teachings of this invention, it has been discovered that it is necessary, in order to obtain a stable, clear gel from a process for making the same that is repeatable and controllable, that the composition further incorporate from about 0.1 to about 5% by weight of a hardening agent. The hardening agent is selected from the group consisting of lower alkanol amines, diamines and amides wherein such amines, diamines and amides comprise at least two such lower alkanol and preferably two to four such groups wherein said alkanol moieties comprise from two to four carbon atoms. Tetrahydroxyalkyldiamine compounds are exemplified by tetrahydroxy propyl ethylene diamine and by the polyoxamines e.g., the polyoxyethylene, polyoxypropylene block copolymers of ethylene diamine. Amides are exemplified by such fatty acid amides as for example, coco diethanol amide and ethanol amides of lauric acid.

In addition to the above ingredients, the reaction mixture may also comprise a large variety of application aids which are added to improve the aesthetics and functionality of the solid gel stick. Such functional characteristic such as emolliency, lubricity, tackiness, lack of brittleness, clarity, etc. may be improved by the addition of such application aids. Examples of such suitable compounds employed are the polyethylene glycol ethers of alkyl alcohols e.g. of stearyl alcohol or the polyoxypropylene polyoxyethylene ethers of alkyl alcohols such as cetyl alcohol which compounds render the stick less brittle and less tacky; compound such as the silicone and lanolin derivatives, isopropyl myristrate or palmitates, polypropylene glycol alkyl ethers, tridecyl octanoate, as emollients and for lubricity; castor oil as a solubilizing agent and to improve clarity; as well as preservatives, perfumes and the like.

In preparing the gel sticks of this invention, the antiperspirant metallic salt is combined with the hardening agent in a solvent capable of dissolving these ingredients together with the complexing agent. The solvent should be a polar solvent such as water or monohydric or polyhydric alcohols e.g. ethyl alcohol, polyethylene glycol glycerine or mixtures thereof. The solvent is preferably present in weight proportions of 40 to 90%, by weight, of the formulation and more preferably 50 to 70% by weight of the formulation. Application aids may be added to this mixture as well as perfumes and coloring agents. Just before it is desired to form the sticks, the appropriate quantity of complexing agent is added to the mixture. After stirring and complete dissolution of the complexing agent, preferably performed at a low temperature of 21° C. or less to prevent premature solidification, the mixture is allowed to deaerate and then is used to fill molds. The filled molds are formed into hardened sticks by placing the molds into a radiant heat chamber at a temperature of 60° C. to 80° C. for a time period of 10 minutes and preferably 20 minutes. The molds are then allowed to cool and annealed for several days prior to use.

DETAILED DESCRIPTION OF THE INVENTION

The invention is illustrated by the following specific examples, wherein all proportions are in parts by weight.

EXAMPLE I

This example gives the basic components of the preferred formulation:

|  | Parts by Weight |
|---|---|
| Part I | |
| H₂O | 72.85 |
| Aluminum Chlorohydrate | 20.00 |
| Tetra Hydroxy Propyl Ethylene Diamine* | 0.20 |
| Part II | |
| Ammonium Acetate | 7.00 |
| | 100.00 |

*Sold by the BASF Corporation under the trade name "Quadrol".

EXAMPLE II

This example gives a more extensive prototype formulation. The formulation includes castor oil as one of the application aids to reduce brittleness.

|  | Parts by Weight |
|---|---|
| Part I | |
| Water | 15.00 |
| Propylene Glycol | 56.80 |
| Aluminum Chlorohydrate | 20.00 |
| Tetra Hydroxy Propyl Ethylene Diamine (Quadrol) | 0.20 |
| Part II | |
| Castor Oil POE 200 (Protechem) CA-ZOO, Protameen Chem. Co.) | 0.50 |
| Part III | |
| Ammonium Acetate | 7.00 |
| Part IV | |
| Perfume | 0.50 |
| Color | |
| | 100.00 |

The composition of Example II results in a relatively hard, stable, solid gel suitable for use in a commercial antiperspirant stick.

COMPARATIVE EXAMPLE

The identical composition to that of Example II is employed to make a gel stick with the exception that the diamine (Quadrol) is eliminated from the formulation. The resulting gel is soft, can be easily penetrated (i.e. with finger pressure) and can be made to flow under the force of gravity. As such, the gel is unusable as a commercial antiperspirant stick.

EXAMPLE III

This example gives the procedure for preparing the gel sticks of this invention. For the formulation of Example II, the water and propylene glycol are mixed in a main mixing vessel. The Quadrol diamine is added and stirred until it is dissolved. The aluminum chlorohydrate is added slowly until completely dissolved and the castor oil is then added to the mixture. The perfume and color are also added. This solution is the stock solution to which the ammonium acetate is added while the solution is maintained at a temperature of 21° C.

The resulting solution is stirred for ten minutes to completely dissolve the ammonium acetate. The mixing is then discontinued and the batch allowed to deaerate. After the batch is deaerated, the mixture is poured into molds and hardened into sticks by placing the molds in a radiant heat chamber at 60° C. to 80° C. for ten to twenty minutes. The molds are allowed to cool and annealed for several days before use. The resulting product is clear and stable.

What is claimed is:

1. A clear, stable gel anti-perspirant stick comprising the reaction product of:
   (a) about 3 to about 30%, by weight, of an anti-perspirant metal salt;
   (b) about 3 to about 15%, by weight, of a complexing agent, said complexing agent being a mono- or di-carboxylic acid having from two to four carbon atoms or a cosmetically acceptable salt thereof;
   (c) about 0.1 to about 5%, by weight, of a hardening agent selected from the group consisting of lower alkanol amines, diamines and amides wherein said amines, diamines and amides comprise at least two alkanol groups, wherein said alkanol moieties comprise from two to four carbon atoms; and
   (d) the remainder solvent for (a), (b) and (c).

2. The gel stick of claim 1 wherein said complexing agent is an organic acid or its salt selected from the groups consisting of acetic acid, propionic acid, oxalic acid, malonic acid, succinic acid and tartaric acid and cosmetically acceptable salts thereof.

3. The gel stick of claim 2 wherein said complexing agent is ammonium acetate.

4. The gel stick of claim 1 wherein said anti-perspirant metal salt is selected from the group consisting of the sulphate, chloride, chlorohydroxide, oxide, formate, lactate, benzyl sulfonate and phenol sulfonate salts of aluminum, zinc, zirconium and mixtures thereof.

5. The gel sticks of claim 4 said anti-perspirant metal salt is aluminum chlorohydrate.

6. The gel stick of claim 1 wherein said hardening agent is selected from the group consisting of dialkanol amine, tri alkanol amine, tetrahydroxy alkyl ethylene diamine, and the dialkanol amides of a fatty acid.

7. The gel stick of claim 6 wherein said hardening agent is tetrahydroxy propyl ethylene diamine.

* * * * *